United States Patent
Kuesters et al.

(10) Patent No.: US 8,084,487 B2
(45) Date of Patent: Dec. 27, 2011

(54) PROCESSES FOR THE PREPARATION OF 4-OXO-OCTAHYDRO-INDOLE-1-CARBOCYCLIC ACID METHYL ESTER AND DERIVATIVES THEREOF

(75) Inventors: Ernst Kuesters, Eschbach (DE); Murat Acemoglu, Basel (CH); Philipp Lustenberger, Basel (CH); Gottfried Sedelmeier, Schallstadt (DE); Beat Schmitz, Allschwil (CH); Gerhard Penn, Oberwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/058,608

(22) PCT Filed: Aug. 10, 2009

(86) PCT No.: PCT/EP2009/060351
§ 371 (c)(1),
(2), (4) Date: Feb. 11, 2011

(87) PCT Pub. No.: WO2010/018154
PCT Pub. Date: Feb. 18, 2010

(65) Prior Publication Data
US 2011/0144352 A1    Jun. 16, 2011

Related U.S. Application Data

(60) Provisional application No. 61/088,156, filed on Aug. 12, 2008.

(51) Int. Cl.
*C07D 209/32* (2006.01)
*C07C 271/24* (2006.01)
*A61K 31/403* (2006.01)

(52) U.S. Cl. ........ 514/418; 514/421; 548/489; 548/484; 548/452; 560/115

(58) Field of Classification Search .................. None
See application file for complete search history.

(56) References Cited

FOREIGN PATENT DOCUMENTS

WO    WO 03/047581    6/2003

OTHER PUBLICATIONS

Dolfini J E et al., "Aziridinyl Compounds as Intermediates in Pyrrolidine Synthesis", Tetrahedron Letters, vol. 6, No. 25, pp. 2053-2058, 1965.
Sepulveda-Arques J et al., "Stereoselective Ring Transformation of N-Alkyl Aziridines into Oxazolidin-2-Ones", vol. 52, No. 6, pp. 2097-2102, 1996.
Fritz H et al., "Synthesis of an undecacyctic di-indoline diether of the dimeric calebas curare alkaloids type", Liebigs Ann. Chem, 715, pp. 135-145, 1968.

*Primary Examiner* — Yong Chu
*Assistant Examiner* — Michael Barker
(74) *Attorney, Agent, or Firm* — Daniel Woods

(57) ABSTRACT

The present invention relates to a process for the production of carbamic acid (2-chloroethyl)(3-oxocyclohexyl)-alkyl ester enantiomers and of 1-carbalkoxy-4-ketoperhydroindole enantiomers.

11 Claims, No Drawings

PROCESSES FOR THE PREPARATION OF 4-OXO-OCTAHYDRO-INDOLE-1-CARBOCYCLIC ACID METHYL ESTER AND DERIVATIVES THEREOF

This application is a 371 of PCT/EP2009/060351 filed on Aug. 10, 2009, which claims benefit of U.S. Provisional Application No. 61/088,156, filed on Aug. 12, 2008, which in their entirety are herein incorporated by reference.

The present invention relates to a process for the production of carbamic acid (2-chloroethyl)(3-oxocyclohexyl)-alkyl ester enantiomers and of 1-carbalkoxy-4-ketoperhydroindole enantiomers.

WO 03/47581 discloses a series of acetylene derivatives having activity towards human metabotropic glutamate receptors (mGluRs). In particular, there is disclosed the compound (3aR,4S,7aR)-4-hydroxy-4-m-tolylethynyl-octahydro-indole-1-carboxylic acid methyl ester, which can be obtained in free base or acid addition salt form and has the formula (I):

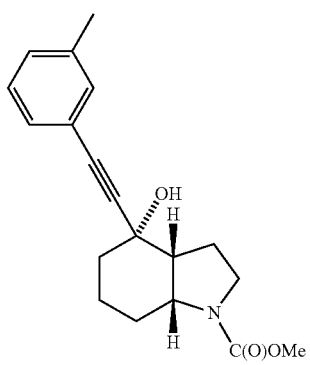

WO 03/47581 also discloses a process for the production of the above compound which involves hydrogenation of a 1,5,6,7-tetrahydroindol-4-one derivative. The hydrogenation step is cumbersome, low yielding and has poor selectivity for the (3aR,4S,7aR) stereoisomer. An undesirable by-product is also formed.

According to the present invention, there is provided an alternative process for the production of a compound of the formula (I) or a pharmaceutically acceptable salt thereof, which comprises reacting 3-ethynyltoluene with a compound of the formula (II) or a salt thereof:

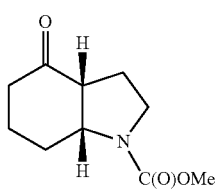

to form the compound of formula (I) and optionally converting the compound of formula (I) to a pharmaceutically acceptable salt.

The above reaction is preferably performed in the presence of a base which promotes deprotonation of the ethynyl group. In an embodiment, the base is an alkyllithium reagent such as n-hexyllithium. The reaction may be performed in an aprotic solvent such as tetrahydrofuran.

A compound of formula (II) may be obtained by cyclisation of a compound of the formula (III) or a salt thereof:

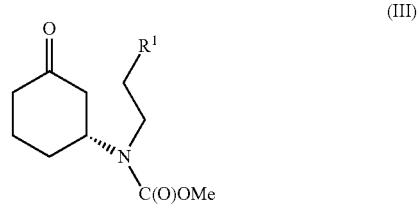

wherein $R^1$ is a leaving group.

Cyclisation may be performed using a base which deprotonates the 2-position of the cyclohexanone ring. By way of example, the base may comprise a mixture of pyrrolidine and triethylamine. The reaction may be performed in an organic solvent such as toluene.

Suitable leaving groups represented by $R^1$ will be apparent to those skilled in the art and include, for example, halo, e.g. chloro, bromo or iodo, tosylates, mesylates, alkylsulphonates, e.g. methanesulfonate, and halosulphonates, e.g. fluorosulphonate.

The compound of formula (III) preferably comprises an excess of the (R) enantiomer as depicted in the formula above, more preferably in a substantially pure form of said enantiomer. In an embodiment, the compound of formula (III) comprises greater than 70%, more preferably greater than 90%, more preferably greater than 95% of the (R) enantiomer. The desired enantiomer may be obtained by resolving an enantiomeric mixture, e.g. a racemic mixture, of a compound of formula (III). In an embodiment, resolution is performed using chiral high performance liquid chromatography (HPLC) involving the use of a chiral stationary phase.

A compound of formula (III) may be obtained by reacting a compound of the formula $R^1C(O)OMe$ with a compound of the formula (IV) or a salt thereof:

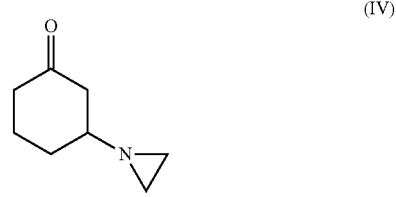

A compound of formula (IV) may be obtained by reacting cyclohexen-2-one with aziridine or a salt thereof. The reaction may be performed in the presence of an organic solvent such as toluene. Suitable procedures are illustrated in the Examples herein.

The invention includes the above processes for making the compound of formula (I) as well as each step thereof and all combinations of sequential steps. As mentioned above, the compound of formula (I) may further be converted to a pharmaceutically acceptable salt form, in particular acid addition salt form. Acid addition salts may be obtained in accordance with known methods, e.g. by addition of acid to the last reaction step or prior to recrystallization.

The invention also relates to the use of the various compounds, e.g. selected from compounds of the formulae (II)

and (III), and their salts, for the production of a compound of formula (I) or a pharmaceutically acceptable salt thereof.

The compound of formula (I) or the intermediate compounds may be purified and/or separated by a conventional manner such as recrystallization, column chromatography, distillation, centrifugal separation, washing or drying.

The compound of formula (I) or a pharmaceutically acceptable salt thereof may be formulated with a pharmaceutically acceptable carrier or diluent, to form a pharmaceutical composition.

Pharmaceutical compositions according to the invention may be compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutical acceptable carrier. The dose of the active ingredient depends on the species of warm-blooded animal, body weight, age and individual condition, individual pharmacokinetic data, the disease to be treated and the mode of administration.

Pharmaceutical compositions may comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

Alternatively compounds may be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The pharmaceutical compositions of the present invention may be prepared in a manner known per se, for example by means of conventional dissolving, lyophilizing, mixing, granulating or confectioning processes.

A compound of formula (I) and pharmaceutically acceptable salts thereof are useful in the treatment of disorders associated with irregularities of the glutamatergic signal transmission, and of nervous system disorders mediated full or in part by mGluR5. Activity towards mGluRs can be determined according to any of the procedures described in WO 03/047581.

Disorders associated with irregularities of the glutamatergic signal transmission are for example epilepsy, cerebral ischemias, especially acute ischemias, ischemic diseases of the eye, muscle spasms such as local or general spasticity and, in particular, convulsions or pain.

Nervous system disorders mediated full or in part by mGluR5 include, for example acute, traumatic and chronic degenerative processes of the nervous system, such as Parkinson's disease, senile dementia, Alzheimer's disease, Huntington's chorea, amyotrophic lateral sclerosis and multiple sclerosis, psychiatric diseases such as schizophrenia and anxiety, depression, pain, itch and drug abuse, e.g. alcohol and nicotine abuse and cocaine use disorders.

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.5 to about 100 mg/kg animal body weight. In larger mammals, for example humans, an indicated daily dosage is in the range from about 5 to 1500 mg, preferably about 10 to about 1000 mg of the compound conveniently administered in divided doses up to 4 times a day or in sustained release form.

A compound of formula (I) can be administered either alone, or in combination with other pharmaceutical agents effective in the treatment of conditions mentioned above.

For the indication pain, compounds of the invention can be used in combination with analgesic agents (opiates) or with non-steroidal anti-inflammatory drugs (NSAIDs) such as Rofecoxib (Vioxx®), Celecoxib (Celebrex®) or Lumiracoxib (Prexige®).

For the indication nicotine use disorders, compounds of the invention can be used in combination with bupropione (Zyban®).

The invention also provides a composition comprising a compound of formula (I) or a pharmaceutically acceptable salt thereof in combination with a relatively minor proportion of one or more intermediate compounds, e.g. selected from compounds of formulae (II), (III) and (IV), and salts thereof.

The following Examples illustrate the invention.

3-(1-aziridinyl) cyclohexanone is synthesized according to literature (J. E. Dolfini et al., Tetrahedron Letters, No 25, pp. 2053-2058, 1965)

EXAMPLE 1-5

Synthesis of Carbamic Acid (2-chloroethyl)(3-oxocyclohexyl)-alkyl ester 21.6 mmol 3-(1-aziridinyl) cyclohexanone are dissolved in 15 ml toluene and cooled down to 0° C. To the clear solution 21.6 mmol alkyl chloroformate are added within 20 minutes (exothermic reaction). The temperature is kept between 0-10° C. The yellowish to brown solution is warmed up to room temperature and stirred for further 1 hour. Solvent and excess reagents are removed under vacuum (60° C./20 mbar) and the remaining oil is treated three times with 5 ml toluene to remove not reacted alky chloroformate under vacuum yielding:
4.95 g carbamic acid (2-chloroethyl)(3-oxocyclohexyl)-methyl ester (example 1)
5.22 g carbamic acid (2-chloroethyl)(3-oxocyclohexyl)-ethyl ester (example 2)
5.53 g carbamic acid (2-chloroethyl)(3-oxocyclohexyl)-propyl ester (example 3)
5.92 g carbamic acid (2-chloroethyl)(3-oxocyclohexyl)-butyl ester (example 4)
6.27 g carbamic acid (2-chloroethyl)(3-oxocyclohexyl)-neopentyl ester (example 5)

EXAMPLE 6-15

Synthesis of (R)- and (S)-carbamic acid (2-chloroethyl)(3-oxocyclohexyl)-alkyl ester 5 g racemic carbamic acid (2-chloroethyl)(3-oxocyclohexyl)-alkyl ester are dissolved in 50 ml heptane/2-propanol=1/1 (V/V) and injected onto a preparative Chiralpak-AD column (particle size: 20 µm, column dimensions: 30 cm length×10 cm I.D.). Using heptane/2-propanol/methanol=90/7.5/2.5 (V/V/V) as the mobile phase at room temperature and a flow rate of 400 ml/min, baseline separation is achieved within 60 min while the R-enantiomer elutes always prior to its S-enantiomer. A second chromatographic run is performed under identical conditions and the corresponding fractions are combined. The solvents are removed under vacuum yielding:

4.6 g (R)-carbamic acid (2-chloroethyl)(3-oxocyclohexyl)-methyl ester (example 6)
$_1$H NMR (500 MHz, DMSO-$d_6$) δ ppm 1.47 (m, 1 H) 1.79 (m, 1 H) 1.92 (m, 2 H) 2.13 (d, J=1.53 Hz, 1 H) 2.25 (m, 1 H) 2.31 (dt, 1 H) 2.81 (br. m., 1 H) 3.49 (t, J=7.17 Hz, 2 H) 3.60 (s, 3 H) 3.61-3.68 (m, 2 H) 3.89-3.98 (m, 1 H)

4.5 g (S)-carbamic acid (2-chloroethyl)(3-oxocyclohexyl)-methyl ester (example 7)
1H NMR (500 MHz, DMSO-$d_6$) δ ppm 1.47 (m, 1 H) 1.79 (m, 1 H) 1.92 (m, 2 H) 2.13 (d, J=1.53 Hz, 1 H) 2.25 (m, 1 H) 2.31 (dt, 1 H) 2.81 (br. m., 1 H) 3.49 (t, J=7.17 Hz, 2 H) 3.60 (s, 3 H) 3.61-3.68 (m, 2 H) 3.89-3.98 (m, 1 H)

4.2 g (R)-carbamic acid (2-chloroethyl)(3-oxocyclohexyl)-ethyl ester (example 8)
1H NMR (500 MHz, DMSO-$d_6$) δ ppm 1.17 (t, J=7.02 Hz, 3 H) 1.47 (m, 1 H) 1.78 (m, 1 H) 1.92 (m, 2 H) 2.12 (dd, J=14.27, 1.91 Hz, 1 H) 2.25 (d, 1 H) 2.31 (dt, J=14.04, 7.02 Hz, 1 H) 2.80 (br. m., 1 H) 3.49 (t, J=7.25 Hz, 2 H) 3.63 (m, 2 H) 3.93 (m, 1 H) 4.05 (q, J=7.02 Hz, 2 H)

4.4 g (S)-carbamic acid (2-chloroethyl)(3-oxocyclohexyl)-ethyl ester (example 9)
1H NMR (500 MHz, DMSO-$d_6$) δ ppm 1.17 (t, J=7.02 Hz, 3 H) 1.47 (m, 1 H) 1.78 (m, 1 H) 1.92 (m, 2 H) 2.12 (dd, J=14.27, 1.91 Hz, 1 H) 2.25 (d, 1 H) 2.31 (dt, J=14.04, 7.02 Hz, 1 H) 2.80 (br. m., 1 H) 3.49 (t, J=7.25 Hz, 2 H) 3.63 (m, 2 H) 3.93 (m, 1 H) 4.05 (q, J=7.02 Hz, 2 H)

3.8 g (R)-carbamic acid (2-chloroethyl)(3-oxocyclohexyl)-propyl ester (example 10)
1H NMR (500 MHz, DMSO-$d_6$) δ ppm 0.88 (t, J=7.40 Hz, 3 H) 1.47 (qt, J=13.49, 3.87 Hz, 1 H) 1.58 (m, J=7.25, 7.00, 7.00, 7.00, 7.00 Hz, 2 H) 1.79 (br. m, 1 H) 1.92 (m, 2 H) 2.12 (m, 1H) 2.25 (br. m, 1 H) 2.29 (dt, J=14.04, 7.02 Hz, 1 H) 2.79 (br. m., 1 H) 3.50 (m, 2 H) 3.63 (m, 2 H) 3.85-4.09 (m, 3 H)

3.8 g (S)-carbamic acid (2-chloroethyl)(3-oxocyclohexyl)-propyl ester (example 11)
1H NMR (500 MHz, DMSO-$d_6$) δ ppm 0.88 (t, J=7.40 Hz, 3 H) 1.47 (qt, J=13.49, 3.87 Hz, 1 H) 1.58 (m, J=7.25, 7.00, 7.00, 7.00, 7.00 Hz, 2 H) 1.79 (br. m, 1 H) 1.92 (m, 2 H) 2.12 (m, 1H) 2.25 (br. m, 1 H) 2.29 (dt, J=14.04, 7.02 Hz, 1 H) 2.79 (br. m., 1 H) 3.50 (m, 2 H) 3.63 (m, 2 H) 3.85-4.09 (m, 3 H)

3.2 g (R)-carbamic acid (2-chloroethyl)(3-oxocyclohexyl)-butyl ester (example 12)
1H NMR (500 MHz, DMSO-$d_6$) δ ppm 0.88 (t, J=7.40 Hz, 3 H) 1.32 (sxt, J=7.42 Hz, 2 H) 1.47 (m, J=13.54, 3.76 Hz, 1 H) 1.55 (m, 2 H) 1.78 (br. m., 1 H) 1.92 (m, 2 H) 2.12 (dd, J=14.19, 1.68 Hz, 1 H) 2.25 (br. m, 1 H) 2.31 (dt, J=14.11, 6.33 Hz, 1 H) 2.81 (br. m., 1 H) 3.49 (t, J=7.17 Hz, 2 H) 3.63 (m, 2 H) 3.93 (m, 1 H) 4.00 (t, J=6.41 Hz, 2 H)

3.4 g (S)-carbamic acid (2-chloroethyl)(3-oxocyclohexyl)-butyl ester (example 13)
1H NMR (500 MHz, DMSO-$d_6$) δ ppm 0.88 (t, J=7.40 Hz, 3 H) 1.32 (sxt, J=7.42 Hz, 2 H) 1.47 (m, J=13.54, 3.76 Hz, 1 H) 1.55 (m, 2 H) 1.78 (br. m., 1 H) 1.92 (m, 2 H) 2.12 (dd, J=14.19, 1.68 Hz, 1 H) 2.25 (br. m, 1 H) 2.31 (dt, J=14.11, 6.33 Hz, 1 H) 2.81 (br. m., 1 H) 3.49 (t, J=7.17 Hz, 2 H) 3.63 (m, 2 H) 3.93 (m, 1 H) 4.00 (t, J=6.41 Hz, 2 H)

4.8 g (R)-carbamic acid (2-chloroethyl)(3-oxocyclohexyl)-neopentyl ester (example 14)
1H NMR (500 MHz, DMSO-$d_6$) δ ppm 0.90 (s, 9 H) 1.47 (m, 1 H) 1.79 (br. m., 1 H) 1.94 (br. m., 2 H) 2.13 (m, 1 H) 2.24 (br. m, 1 H) 2.31 (dt, J=14.04, 6.10 Hz, 1 H) 2.82 (br. m, 1 H) 3.52 (t, J=7.17 Hz, 2 H) 3.64 (m, 2 H) 3.73 (br. m., 2 H) 3.94 (m, 1 H)

5.2 g (S)-carbamic acid (2-chloroethyl)(3-oxocyclohexyl)-neopentyl ester (example 15)
1H NMR (500 MHz, DMSO-$d_6$) δ ppm 0.90 (s, 9 H) 1.47 (m, 1 H) 1.79 (br. m., 1 H) 1.94 (br. m., 2 H) 2.13 (m, 1 H) 2.24 (br. m, 1 H) 2.31 (dt, J=14.04, 6.10 Hz, 1 H) 2.82 (br. m, 1 H) 3.52 (t, J=7.17 Hz, 2 H) 3.64 (m, 2 H) 3.73 (br. m., 2 H) 3.94 (m, 1 H)

EXAMPLE 16-20

Synthesis of 1-carbalkoxy-4-ketoperhydroindole 15 mmol carbamic acid (2-chloroethyl)(3-oxocyclohexyl)-alkyl ester are dissolved in 15 ml methylene chloride. To the orange coloured solution 1.07 g pyrrolidine and 1.52 g triethylamine are added. The reaction mixture is stirred 16 h at room temperature and finally diluted with 45 ml isopropyl acetate and 30 ml of water. Under stirring the pH of the emulsion is adjusted to pH=2 and stirring is continued for further 30 min. After phase separation the aqueous phase is extracted two times with 20 ml isopropyl acetate and the combined organic phase is washed three times with 20 ml water each. The solvent is removed under vacuum (50° C./20 mbar) yielding:

2.55 g 1-carbmethoxy-4-ketoperhydroindole (example 16)
2.70 g 1-carbethoxy-4-ketoperhydroindole (example 17)
2.98 g 1-carbpropoxy-4-ketoperhydroindole (example 18)
3.15 g 1-carbbutoxy-4-ketoperhydroindole (example 19)
3.34 g 1-carbneopentoxy-4-ketoperhydroindole (example 20)

EXAMPLE 21-30

Synthesis of (S,S)- and (R,R)-1-carbalkoxy-4-ketoperhydroindole 5 g racemic 1-carbalkoxy-4-ketoperhydroindole are dissolved in 50 ml heptane/2-propanol=1/1 (V/V) and injected onto a preparative Chiralpak-AD column (particle size: 20 □m, column dimensions: 30 cm length×10 cm I.D.). Using heptane/2-propanol/methanol=90/7.5/2.5 (V/V/V) as the mobile phase at room temperature and a flow rate of 400 ml/min, baseline separation is achieved within 60 min while the S,S-enantiomer elutes always prior to its R,R-enantiomer. The solvents are removed under vacuum yielding:

2.5 g (S,S)-1-carbmethoxy-4-ketoperhydroindole (example 21)
1H NMR (500 MHz, DMSO-$d_6$) δ ppm 1.58 (br. m., 2 H) 1.73 (br. m., 1 H) 1.88 (m, 1H) 2.01 (m, 1 H) 2.14 (m, 1 H) 2.19 (m, 1H) 2.37 (td, J=10.76, 5.65 Hz, 1 H) 2.82 (m, 1 H) 3.29 (m, 2 H) 3.57 (s, 3 H) 4.04 (m, 1 H)

2.4 g (R,R)-1-carbmethoxy-4-ketoperhydroindole (example 22)
1H NMR (500 MHz, DMSO-$d_6$) δ ppm 1.58 (br. m., 2 H) 1.73 (br. m., 1 H) 1.88 (m, 1 H) 2.01 (m, 1 H) 2.14 (m, 1 H) 2.19 (m, 1H) 2.37 (td, J=10.76, 5.65 Hz, 1 H) 2.82 (m, 1 H) 3.29 (m, 2 H) 3.57 (s, 3 H) 4.04 (m, 1 H)

1.5 g (S,S)-1-carbethoxy-4-ketoperhydroindole (example 23)
1H NMR (500 MHz, DMSO-$d_6$) δ ppm 1.16 (t, J=7.10 Hz, 3 H) 1.57 (m, 2 H) 1.75 (br. m., 1 H) 1.88 (m, 1 H) 2.02 (d, J=4.58 Hz, 1 H) 2.13 (m, 1 H) 2.19 (m, 1H) 2.38 (td, J=10.64, 5.57 Hz, 1 H) 2.83 (m, 1 H) 3.28 (m, 2 H) 4.03 (m, 3 H)

2.4 g (R,R)-1-carbethoxy-4-ketoperhydroindole (example 24)
1H NMR (500 MHz, DMSO-$d_6$) δ ppm 1.16 (t, J=7.10 Hz, 3 H) 1.57 (m, 2 H) 1.75 (br. m., 1 H) 1.88 (m, 1 H) 2.02 (d, J=4.58 Hz, 1 H) 2.13 (m, 1 H) 2.19 (m, 1H) 2.38 (td, J=10.64, 5.57 Hz, 1 H) 2.83 (m, 1 H) 3.28 (m, 2 H) 4.03 (m, 3 H)

2.3 g (S,S)-1-carbpropoxy-4-ketoperhydroindole (example 25)
1H NMR (500 MHz, DMSO-$d_6$) δ ppm 0.88 (t, J=7.40 Hz, 3 H) 1.56 (m, 4 H) 1.76 (br. m., 1 H) 1.88 (m, 1 H) 2.02 (m, 1

H) 2.14 (br. m, 1H) 2.05 (m, 1 H) 2.36 (dt, J=10.68, 5.34 Hz, 1 H) 2.83 (m, 1 H) 3.29 (m, 2 H) 3.93 (m, 2 H) 4.04 (m, 1 H)

2.1 g (R,R)-1-carbpropoxy-4-ketoperhydroindole (example 26)

1H NMR (500 MHz, DMSO-$d_6$) δ ppm 0.88 (t, J=7.40 Hz, 3 H) 1.56 (m, 4 H) 1.76 (br. m., 1 H) 1.88 (m, 1 H) 2.02 (m, 1 H) 2.14 (br. m, 1H) 2.05 (m, 1 H) 2.36 (dt, J=10.68, 5.34 Hz, 1 H) 2.83 (m, 1 H) 3.29 (m, 2 H) 3.93 (m, 2 H) 4.04 (m, 1 H)

2.3 g (S,S)-1-carbbutoxy-4-ketoperhydroindole (example 27)

1H NMR (500 MHz, DMSO-$d_6$) δ ppm 0.88 (t, J=7.40 Hz, 3 H) 1.32 (dq, J=14.97, 7.42 Hz, 2 H) 1.54 (m, 4 H) 1.75 (br. m., 1 H) 1.88 (m, 1 H) 2.02 (m, 1 H) 2.13 (br. m, 1 H) 2.19 (m, 1H) 2.73 (dt, J=10.83, 5.42 Hz, 1 H) 2.83 (m, 1 H) 3.29 (m, 2 H) 3.99 (m, 3 H)

2.0 g (R,R)-1-carbbutoxy-4-ketoperhydroindole (example 28)

1H NMR (500 MHz, DMSO-$d_6$) δ ppm 0.88 (t, J=7.40 Hz, 3 H) 1.32 (dq, J=14.97, 7.42 Hz, 2 H) 1.54 (m, 4 H) 1.75 (br. m., 1 H) 1.88 (m, 1 H) 2.02 (m, 1 H) 2.13 (br. m, 1 H) 2.19 (m, 1H) 2.73 (dt, J=10.83, 5.42 Hz, 1 H) 2.83 (m, 1 H) 3.29 (m, 2 H) 3.99 (m, 3 H)

1.7 g (S,S)-1-carbneopentoxy-4-ketoperhydroindole (example 29)

1H NMR (500 MHz, DMSO-$d_6$) δ ppm 0.90 (s, 9 H) 1.59 (m, 2 H) 1.75 (br. sm, 1 H) 1.90 (m, 1 H) 2.03 (m, 1 H) 2.14 (br. M, 1H) 2.20 (m, 1 H) 2.36 (dt, J=10.83, 5.34 Hz, 1 H) 2.84 (m, 1 H) 3.33 (m, 2 H) 3.68 (br. m, 2 H) 4.07 (br. m., 1 H)

1.5 g (R,R)-1-carbneopentoxy-4-ketoperhydroindole (example 30)

1H NMR (500 MHz, DMSO-$d_6$) δ ppm 0.90 (s, 9 H) 1.59 (m, 2 H) 1.75 (br. sm, 1 H) 1.90 (m, 1 H) 2.03 (m, 1 H) 2.14 (br. M, 1H) 2.20 (m, 1 H) 2.36 (dt, J=10.83, 5.34 Hz, 1 H) 2.84 (m, 1 H) 3.33 (m, 2 H) 3.68 (br. m, 2 H) 4.07 (br. m., 1 H)

The invention claimed is:

1. A process for the production of a compound of the formula (I) or a pharmaceutically acceptable salt thereof:

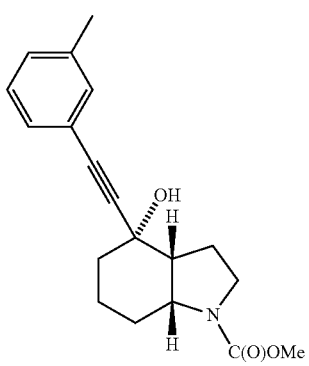

(I)

which comprises reacting 3-ethynyltoluene with a compound of the formula (II) or a salt thereof:

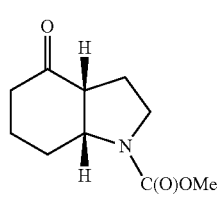

(II)

to form the compound of formula (I) and optionally converting the compound of formula (I) to a pharmaceutically acceptable salt.

2. A process according to claim 1, wherein the compound of formula (II) is obtained by cyclisation of a compound of the formula (III) or a salt thereof:

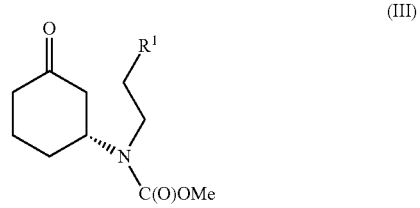

(III)

wherein $R^1$ is a leaving group.

3. A process according to claim 2, wherein the compound of formula (III) is obtained by reacting a compound of the formula $R^1C(O)OMe$ with a compound of the formula (IV) or a salt thereof:

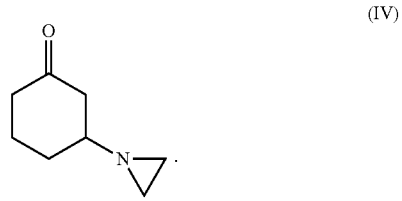

(IV)

4. A process according to claim 3, wherein the compound of formula (IV) is obtained by reacting cyclohexen-2-one with aziridine or a salt thereof.

5. A process according to claim 1, which further comprises formulating the compound of formula (I) into a pharmaceutical composition.

6. A process for the production of a compound of the formula (II) or a salt thereof:

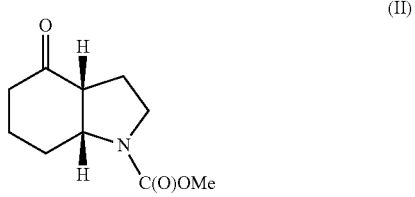

(II)

which comprises cyclisation of a compound of the formula (III) or a salt thereof:

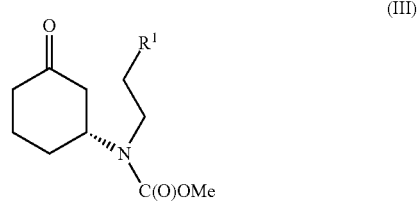

(III)

wherein $R^1$ is a leaving group.

7. A process according to claim 6, wherein the compound of formula (III) is obtained according to claim 3 or claim 4.

8. A process for the production of a compound of the formula (III) or a salt thereof:

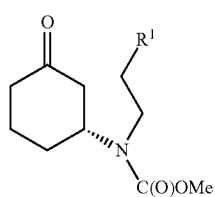

(III)

wherein R¹ is a leaving group;
which comprises reacting a compound of the formula R¹C(O)OMe with a compound of the formula (IV) or a salt thereof:

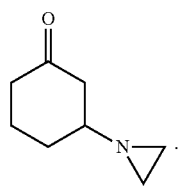

(IV)

9. A process according to claim 8, wherein the compound of formula (IV) is obtained according to claim 4.

10. A compound of the formula (II) or a salt thereof:

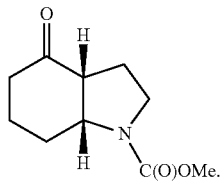

(II)

11. A compound of the formula (III) or a salt thereof:

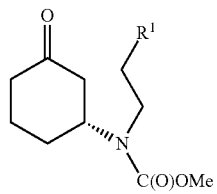

(III)

wherein R¹ is a leaving group.

* * * * *